United States Patent [19]

Eller et al.

[11] Patent Number: 5,780,680
[45] Date of Patent: Jul. 14, 1998

[54] PREPARATION OF AMINES FROM OLEFINS OVER MESOPOROUS OXIDES HAVING A HIGH SURFACE AREA

[75] Inventors: Karsten Eller, Ludwigshafen; Rudolf Kummer, Frankenthal; Ulrich Müller, Neustadt, all of Germany

[73] Assignee: BASF Aktiengesellschaft, Ludwigschafen, Germany

[21] Appl. No.: 839,800

[22] Filed: Apr. 18, 1997

[30] Foreign Application Priority Data

Apr. 19, 1996 [DE] Germany .................. 196 15 482.0

[51] Int. Cl.$^6$ .................. C07C 209/60
[52] U.S. Cl. .................. 564/485
[58] Field of Search .................. 564/485

[56] References Cited

U.S. PATENT DOCUMENTS

| | | | |
|---|---|---|---|
| 4,375,002 | 2/1983 | Peterson et al. | 564/445 |
| 4,536,602 | 8/1985 | Deeba | 564/485 |
| 5,057,296 | 10/1991 | Beck | 423/277 |
| 5,648,546 | 7/1997 | Bergfeld et al. | 564/485 |

FOREIGN PATENT DOCUMENTS

| | | |
|---|---|---|
| 2092964 | 6/1994 | Canada . |
| 132 736 | 7/1984 | European Pat. Off. . |
| 133 938 | 7/1984 | European Pat. Off. . |
| 101 921 | 4/1986 | European Pat. Off. . |
| 431 451 | 11/1990 | European Pat. Off. . |
| 469 719 | 2/1992 | European Pat. Off. . |
| 752 409 | 6/1996 | European Pat. Off. . |
| 42 06 992 | 3/1992 | Germany . |
| 44 07 326 | 3/1994 | Germany . |
| 44 31 093 | 9/1994 | Germany . |
| 04082864 | 3/1992 | Japan . |
| 91/11390 | 8/1991 | WIPO . |

OTHER PUBLICATIONS

Beck et al., *J. Am. Chem. Soc.*, vol. 114, 1992, pp. 10834–10843.
Brunet et al., *J. of Mol. Cat.*, vol. 49, 1988, pp. 235–259.
Gontier et al., *Zeolites*, vol. 15, No. 7, Oct. 1995, pp. 601–610.
Bagshaw et al., *Science*, vol. 269, Sep. 1, 1995, pp. 1242–1244.
Corma et al., *Studies in Surface Science and Catalysis*, vol. 37, Sept. 1987, pp. 495–503.

*Primary Examiner*—Brian M. Burn
*Attorney, Agent, or Firm*—Keil & Weinkauf

[57] ABSTRACT

In a process for preparing amines of the formula I

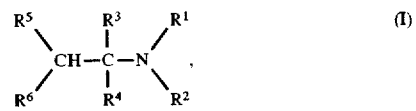

where
$R^1, R^2, R^3, R^4, R^5, R^6$ are hydrogen, $C_1$–$C_{20}$-alkyl, $C_2$–$C_{20}$-alkenyl, $C_2$–$C_{20}$-alkynyl, $C_3$–$C_{20}$-cycloalkyl, $C_4$–$C_{20}$-alkyl-cycloalkyl, $C_4$–$C_{20}$-cycloalkyl-alkyl, aryl, $C_7$–$C_{20}$-alkylaryl or $C_7$–$C_{20}$-aralkyl, $R^1$ and $R^2$ together form a saturated or unsaturated, divalent $C_3$–$C_9$-alkylene chain and $R^3$ and $R^5$ are $C_{21}$–$C_{200}$-alkyl, $C_{21}$–$C_{200}$-alkenyl or together form a divalent $C_2$–$C_{12}$-alkylene chain, by reating olefins of the formula II

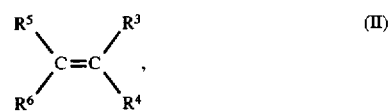

where $R^3$, $R^4$, $R^5$ and $R^6$ are as defined above, with ammonia or primary or secondary amines of the formula III

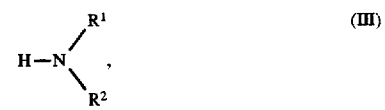

where $R^1$ and $R^2$ are as defined above, at from 200° to 350° C. and a pressure of from 100 to 300 bar in the presence of a heterogeneous catalyst, the heterogeneous catalysts being mesoporous oxides having a high surface area.

11 Claims, No Drawings

PREPARATION OF AMINES FROM OLEFINS OVER MESOPOROUS OXIDES HAVING A HIGH SURFACE AREA

BACKGROUND OF THE INVENTION

1. Field of the Invention

The present invention relates to a process for preparing amines by reacting ammonia or primary or secondary amines with olefins at elevated temperatures and pressures in the presence of mesoporous oxides having a high surface area.

2. Description of Related Art

A review of the methods for aminating olefins is given in "Functionalisation of Alkenes: Catalytic Amination of Monoolefins", J. J. Brunet et al. J.Mol.Catal., 49 (1989), pages 235 to 259.

There are two fundamental catalytic mechanisms. The olefin is coordinated via a metal complex and this activated species can be attacked by the nucleophilic amine and form a higher aminated product. The amine can be chemisorbed on acid centers or metal centers (via metal amides) and in this activated form can be reacted with the olefin.

Well-suited catalysts are zeolites. They have a large number of catalytically active centers combined with a high surface area. The zeolites described differ in type and in after-treatment (eg. thermal treatment, dealumination, acid treatment, metal ion exchange, etc.). Examples may be found in U.S. Pat. No. 4,536,602, EP-A-101 921 or DE-A-42 06 992.

EP-A-133 938, EP-A-431 451 and EP-A-132 736 disclose processes in which boron, gallium, aluminum and iron silicate zeolites are used for the preparation of amines from olefins and refer to the possibility of doping these zeolites with alkali metals, alkaline earth metals and transition metals.

CA-A-2 092 964 discloses a process for preparing amines from olefins in which BETA-zeolites, which are defined as crystalline aluminosilicates having a defined composition and a pore size of more than 5 Å, are used. Preference is given to using metal- or acid-modified beta-zeolites.

A particular disadvantage of the zeolites as catalysts is their complicated preparation and thus their high price. The selective synthesis of a molecular sieve (eg. of zeolites) by hydrothermal synthesis requires precise control of many parameters, for instance the crystallization time, the crystallization temperature, the pressure or the aging steps. The structure-directing compound (template) customarily used in a zeolite synthesis has to be removed after crystallization. The removal of the template is generally carried out by calcination, with the organic compound being oxidatively degraded. For ecological and economical reasons, this is a very negative point.

The production of crystals of a certain size or morphology and the preparation of supported zeolites which would often be desirable as catalysts owing to their technical process advantages are generally only possible at great expense, if at all. Zeolites have a very narrow pore size distribution. The pore sizes vary from 4 to about 12 Å depending on zeolite type.

In a zeolite-catalyzed reaction, only molecules which are smaller than the pore dimensions have access to the catalytically active centers in the interior of the zeolite. Reactants having larger dimensions are kept out of the interior of the pores.

For the abovementioned amination reactions, this means that the catalytic centers in the interior of the zeolites are not available for the preparation of amines which are larger than the pore diameter.

The use of acid-modified montmorillonites is described in EP-A-469 719. The use of precipitated catalysts comprising a combination of two or more metal oxides, with the exception of the combination Si and Al, is disclosed in JP-04082864.

DE-A-44 31 093 discloses oxidic catalysts which are prepared via the sol-gel-process. However, the BET surface area of the gels is at most 670 $m^2g^{-1}$ and is thus significantly below the BET surface area of the present mesoporous gels. In addition, the formation of the gels is a metastable process and scaling up is therefore very difficult.

All processes for synthesizing amines from olefins over non-zeolytic catalysts give a low amine yield or a low space-time yield, or lead to rapid deactivation of the catalysts.

SUMMARY OF THE INVENTION

It is an object of the present invention to remedy the above disadvantages, in particular to find catalysts for the amination of olefins whose preparation is significantly simpler than that of the zeolite catalysts and which have a favorable pore size distribution for even relatively bulky amine molecules.

We have found that this object is achieved by a new and improved process for preparing amines of the general formula I

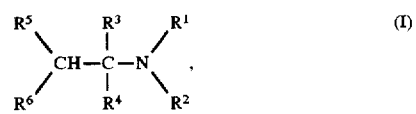

where $R^1, R^2, R^3, R^4, R^5, R^6$ are hydrogen, $C_1$–$C_{20}$-alkyl, $C_2$–$C_{20}$-alkenyl, $C_2$–$C_{20}$-alkynyl, $C_3$–$C_{20}$-cycloalkyl, $C_4$–$C_{20}$-alkyl-cycloalkyl, $C_4$–$C_{20}$-cycloalkyl-alkyl, aryl, $C_7$–$C_{20}$-alkylaryl or $C_7$–$C_{20}$-aralkyl, $R^1$ and $R^2$ together form a saturated or unsaturated, divalent $C_3$–$C_9$-alkylene chain and $R^3$ and $R^5$ are $C_{21}$–$C_{200}$-alkyl, $C_{21}$–$C_{200}$-alkenyl or together form a divalent $C_2$–$C_{12}$-alkylene chain, by reacting olefins of the general formula II

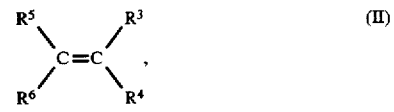

where $R^3$, $R^4$, $R^5$ and $R^6$ are as defined above, with ammonia or primary or secondary amines of the general formula III

where $R^1$ and $R^2$ are as defined above, at from 200° to 350° C. and a pressure of from 100 to 300 bar in the presence of a heterogeneous catalyst, wherein the heterogeneous catalysts used are mesoporous oxides having a high surface area.

DESCRIPTION OF THE PREFERRED EMBODIMENTS

The process of the present invention can be carried out as follows:

The olefin II and ammonia or the primary or secondary amine III can be reacted, for example in a pressure reactor, at from 200° to 350° C., preferably from 220° to 330° C., particularly preferably from 230° to 320° C., and at pressures of from 100 to 300 bar, preferably from 120 to 300 bar, particularly preferably from 140 to 290 bar, in the presence of mesoporous oxides having a high surface area as catalyst, and the amine obtained is preferably separated off and the unreacted starting materials are recirculated.

The present process gives a very good yield with high selectivity and with a high space-time yield. In addition, the deactivation of the catalyst has been suppressed. The catalysts are prepared in a simple and readily reproducible way.

The process of the present invention achieves, even when using a low excess of ammonia or amine, a high selectivity of desired reaction product and the dimerization and/or oligomerization of the olefin used is avoided.

In one embodiment of this process, ammonia and/or amine III is mixed with the olefin II in a molar ratio of from 1:1 to 5:1 and is fed to a fixed-bed reactor and reacted in the gas phase or in a supercritical state at a pressure of from 100 to 300 bar and at from 200° to 350° C.

The desired product can be obtained from the product mixture from the reaction by means of known methods, for example distillation or extraction, and, if need be, brought to the desired purity by means of further separation operations. The unreacted starting materials are preferably returned to the reactor.

It is possible to use monounsaturated or polyunsaturated olefins II, in particular those having from 2 to 10 carbon atoms, or mixtures thereof and polyolefins as starting materials. Owing to the less pronounced tendency to polymerize, monoolefins are more suitable than diolefins and polyolefins, but the latter can be reacted just as selectively with the aid of higher excesses of ammonia or amine. The position of the equilibrium and thus the conversion to the desired amine is very strongly dependent on the reaction pressure selected. High pressure favors the addition product, although the pressure range up to 300 bar generally represents the optimum for technical and economic reasons. The selectivity of the reaction is influenced to a great extent by the temperature, as well as parameters such as ammonia/amine excess and catalyst. Although the reaction rate of the addition reaction increases strongly with rising temperature, competing cracking and recombination reactions of the olefin are promoted at the same time. In addition, an increase in temperature is not advantageous from a thermodynamic point of view. The position of the temperature optimum in respect of conversion and selectivity is dependent on the constitution of the olefin, the amine used and the catalyst and is usually in the range from 200° to 350° C.

Catalysts suitable for the amination of olefins are mesoporous oxides having a high surface area. In an isotherm measured by means of nitrogen adsorption (77 K), these oxides have a characteristic step in the relative pressure range of $p/p^0$=0.2-0.4. Transmission electron microscopy confirms the presence of mesopores in the range from 2 to 6 nm and, in addition, X-ray crystallographic reflections in the 2-theta range from 2° to 6° are observed. Apart from mesopores, the catalysts of the present invention can also contain micropores and the pore size distribution, eg. measured by means of the nitrogen isotherms, is then bimodal. The achievable surface areas for the catalysts of the present invention in powder form are from 400 to 1400 $m^2g^{-1}$, preferably from 500 to 1250 $m^2g^{-1}$, particularly preferably from 700 to 1250 $m^2g^{-1}$ (determined by the BET method) and for the catalysts in extruded form are, depending on the binder content, from 250 to 900 $m^2g^{-1}$, preferably from 300 to 900 $m^2g^{-1}$, particularly preferably from 350 to 900 $m^2g^{-1}$.

The mesoporous oxides can be prepared from readily soluble precursors or the oxides, for example by acid or alkaline hydrolysis of their metal salts or alkoxides with simultaneous addition of anionic, cationic or nonionic surfactants, for instance $C_8$–$C_{16}$-trimethylammonium salts in the form of the chlorides or bromides, or $C_{18}$–$C_{16}$-amines with addition of HCl (Gontier and Tuel; Zeolites 15 (1995), pages 601 to 610). Likewise, polyethylene oxides can be employed as templates (Bagshaw et al., Science 269 (1995), pages 1242 to 1244). The mesoporous oxides are here formed over a period of from a few hours to a number of days at from room temperature to 180° C. After drying, the organic template compounds can be removed by means of a calcination step at from 350° to 650° C. in air and the mesoporous oxides having high surface areas are thus obtained.

The catalysts of the present invention also include mesoporous oxides having a high surface area and a regular hexagonal arrangement of the pores which have become known under the names MCM-41 or M41S. They can also be prepared, if desired, by means of a hydrothermal crystallization step.

Advantageous mesoporous oxides are those composed of one or more oxides selected from the group consisting of $SiO_2$, $Al_2O_3$, $B_2O_3$, $Ga_2O_3$, $In_2O_3$, $TiO_2$, $ZrO_2$, $Nb_2O_5$, $Fe_2O_3$, $GeO_2$, $SnO_2$, $CeO_2$ or $ThO_2$, in particular from the group consisting of $SiO_2$, $Al_2O_3$, $B_2O_3$ and $TiO_2$, and described, for example, in U.S. Pat. No. 5,057,296 or DE-A-44 07 326; particular preference is given to $SiO_2$ as the sole oxide or main constituent of the mesoporous oxides.

The novel mesoporous oxides having a high surface area can be shaped as such or else together with a binder in a weight ratio of from 98:2 to 40:60% by weight to form extrudates or pellets. Suitable binders are various aluminum oxides, preferably boehmite, amorphous aluminosilicates having an $SiO_2/Al_2O_3$ ratio of from 25:75 to 95:5, silicon dioxide, preferably finely divided $SiO_2$, mixtures of finely divided $SiO_2$ and finely divided $Al_2O_3$, finely divided $TiO_2$ and clays. After shaping, the extrudates or compacts are advantageously dried at 110° C. for 16 hours and calcined at from 200° to 500° C. for from 2 to 16 hours. The calcination can also be carried out directly (in situ) in the amination reactor.

To increase the selectivity, the operating life and the number of possible regenerations, the novel mesoporous oxides having a high surface area can be modified in various ways.

One modification of the catalysts comprises doping or ion-exchanging the unshaped or shaped mesoporous oxides having a high surface area with transition metals such as Ti, Zr, Mn, Fe, Mo, Cu, Zn, Cr, noble metals and/or rare earth metals such as La, Ce or Y.

An advantageous embodiment comprises placing the shaped novel mesoporous oxides having a high surface area in a flow tube and passing, for example, a halide or a nitrate of the above-described metals in dissolved form over them at from 20° to 100° C. Such an ion exchange can be carried out, for example, on the hydrogen, ammonium or alkali metal form of the novel mesoporous oxides having a high surface area.

A further possible way of applying the metal to the novel mesoporous oxides having a high surface area is to impregnate the material, for example, with a halide, a nitrate or an oxide of the above-described metals in aqueous or alcoholic solution.

Either an ion exchange or an impregnation can follow a drying, if desired a subsequent calcination. In the case of metal-doped mesoporous oxides having a high surface area, further treatment with hydrogen and/or with water vapor can be favorable.

A further possible way of carrying out the modification is to subject the novel mesoporous oxide having a high surface area, shaped or unshaped, to a treatment with acids such as hydrochloric acid (HCl), hydrofluoric acid (HF), sulfuric acid ($H_2SO_4$), oxalic acid ($HO_2C-CO_2H$) or phosphoric acid ($H_3PO_4$).

A particular embodiment comprises treating the novel mesoporous oxides having a high surface treatment prior to shaping with one of the specified acids in a concentration of from 0.001N to 2N, preferably from 0.05N to 0.5N, for from 1 to 100 hours under reflux. After filtration and washing, the mesoporous oxides are generally dried at from 100° to 160° C. and calcined at from 200° to 600° C. A further particular embodiment comprises an acid treatment of the novel mesoporous oxides having a high surface area with binders after shaping. Here, the mesoporous oxide of the present invention is generally treated for from 1 to 3 hours at from 60° to 80° C. with a 3–25% strength acid, in particular with a 12–20% strength acid, subsequently washed, dried at from 100° to 160° C. and calcined at from 200° to 600° C.

Another possible way of carrying out the modification is given by an exchange with ammonium salts, eg. with $NH_4Cl$, or with monoamines, diamines or polyamines. Here, the mesoporous oxide which is shaped together with a binder is generally exchanged continuously for 2 hours at from 60° to 80° C. with a 10–25% strength, preferably 20% strength, $NH_4Cl$ solution in a weight ratio of oxide/ammonium chloride solution of 1:15 and then dried at from 100° to 120° C.

A further modification which can be carried out on the novel mesoporous oxides having a high surface area is a dealumination in which part of any aluminum atoms present are replaced by silicon or the aluminum content of the oxides is reduced by, for example, hydrothermal treatment. A hydrothermal dealumination is advantageously followed by an extraction with acids or complexing agents in order to remove non-lattice aluminum formed. The replacement of aluminum by silicon can be carried out, for example, by means of $(NH_4)_2SiF_6$ or $SiCl_4$. Examples of dealuminations may be found in Corma et al., Stud. Surf. Sci. Catal. 37 (1987), pages 495 to 503.

The catalysts can be used for the amination of the olefins in the form of extrudates having diameters of, for example, from 1 to 4 mm or as pellets having diameters of, for example, from 3 to 5 mm.

A material suitable for use in fluidized beds and having a particle size of from 0.1 to 0.8 mm can be obtained by milling and sieving the catalyst shaped, for example, into extrudates.

The substituents $R^1$, $R^2$, $R^3$, $R^4$, $R^5$ and $R^6$ in the compounds I, II and III have the following meanings:

$R^1, R^2, R^3, R^4, R^5, R^6$ hydrogen, $C_1$–$C_{20}$-alkyl, preferably $C_1$–$C_{12}$-alkyl, particularly preferably $C_1$–$C_8$-alkyl such as methyl, ethyl, n-propyl, iso-propyl, n-butyl, iso-butyl, sec-butyl, tert-butyl, n-pentyl, iso-pentyl, n-hexyl, iso-hexyl, n-heptyl, iso-heptyl, n-octyl and iso-octyl.

$C_2$–$C_{20}$-alkenyl, preferably $C_2$–$C_{12}$-alkenyl, particularly preferably $C_2$–$C_8$-alkenyl such as vinyl and allyl.

$C_2$–$C_{20}$-alkynyl, preferably $C_2$–$C_8$-alkynyl, in particular $C_2H$ and propargyl, $C_3$–$C_{20}$-cycloalkyl, preferably $C_3$–$C_{12}$-cycloalkyl, particularly preferably $C_5$–$C_8$-cycloalkyl such as cyclopentyl, cyclohexyl, cycloheptyl and cyclooctyl, $C_4$–$C_{20}$-alkyl-cycloalkyl, preferably $C_4$–$C_{12}$-alkyl-cycloalkyl, particularly preferably $C_5$–$C_{10}$-alkyl-cycloalkyl, $C_4$–$C_{20}$-cycloalkyl-alkyl, preferably $C_4$–$C_{12}$-cycloalkyl-alkyl, particularly preferably $C_5$–$C_{10}$-cycloalkyl-alkyl, aryl such as phenyl, 1-naphthyl and 2-naphthyl, preferably phenyl, $C_7$–$C_{20}$-alkylaryl, preferably $C_7$–$C_6$- alkylaryl, particularly preferably $C_7$–$C_{12}$-alkylphenyl such as 2-methylphenyl, 3-methylphenyl, 4-methylphenyl, 2-ethylphenyl, 3-ethylphenyl and 4-ethylphenyl, $C_7$–$C_{20}$-aralkyl, preferably $C_7$–$C_{16}$-aralkyl, particularly preferably $C_7$–$C_{12}$-phenalkyl such as phenylmethyl, 1-phenylethyl, 2-phenylethyl, $R^1$ and $R^2$
together a saturated or unsaturated, divalent $C_3$–$C_9$-alkylene chain, preferably —$(CH_2)_4$—, —$(CH_2)_5$—, —$(CH_2)_7$— and —CH=CH—CH=CH—, $R^3$ or $R^5$ $C_{21}$–$C_{200}$-alkyl, preferably $C_{40}$–$C_{200}$-alkyl, such as polybutyl, polyisobutyl, polypropyl, polyisopropyl and polyethyl, particularly preferably polybutyl and polyisobutyl, $C_{21}$–$C_{200}$-alkenyl, preferably $C_{40}$–$C_{200}$-alkenyl, particularly preferably $C_{70}$–$C_{170}$-alkenyl, $R^3$ and $R^5$
together a divalent $C_2$–$C_{12}$-alkylene chain, preferably a divalent $C_3$–$C_8$-alkylene chain, particularly preferably —$(CH_{12})_3$—, —$(CH_2)_4$—, —$(CH_2)_5$—, —$(CH_2)_6$— and —$(CH_2)_7$—, in particular —$(CH_2)_3$— and —$(CH_2)_4$—.

EXAMPLES

Catalyst syntheses

Catalyst A: Si-B-MPO

A 10 l flask was charged with 504 g of tetraethyl orthosilicate ($Si(OC_2H_5)_4$), 3.24 g of trimethyl borate ($B(OCH_3)_3$), 146.4 g of isopropanol and 720 g of ethanol and the mixture was homogenized for 30 minutes. A mixture of 120 g of dodecylamine, 1560 g of distilled water and 17.5 g of 10% strength hydrochloric acid was slowly added dropwise while stirring over a period of 30 minutes. The resulting white suspension was stirred for 20 hours at about 300 rpm, filtered and the solid was washed with distilled water until neutral. After drying for 24 hours at 60° C., the product was calcined for 10 hours at 500° C. The powder had a BET surface area of 1084 $m^2g^{-1}$.

60 g of the Si-B oxide were compacted together with 40 g of boehmite and 2 g of formic acid in a kneader and kneaded for 45 minutes with addition of water (124 ml). 2 mm extrudates were produced on a ram extruder at a pressing pressure of 40 bar and these were dried for 4 hours at 120° C. and calcined for 16 hours at 500° C.

The finished extrudates had a BET surface area of 794 $m^2g^{-1}$ and a distinctly bimodal pore size distribution with maxima at about 23 Å and about 60 Å.

Catalyst B: Si-MPO

A 10 l flask was charged with 505 g of tetraethyl orthosilicate ($Si(OC_2H_5)_4$), 146.4 g of isopropanol and 720 g of ethanol and the mixture was homogenized for 30 minutes. A mixture of 120 g of dodecylamine, 1560 g of distilled water and 17.5 g of 10% strength hydrochloric acid was slowly added dropwise while stirring over a period of 30 minutes. The resulting white suspension was stirred for 20 hours at about 300 rpm, filtered and the solid was washed with distilled water until neutral.

After drying for 24 hours at 60° C. the product was calcined for 5 hours at 500° C. The powder had a BET surface area of 920 m²g⁻¹.

70 g of the silicon oxide were compacted together with 46 g of boehmite and 2 g of formic acid in a kneader and kneaded for 60 minutes with addition of water (136 ml). 2 mm extrudates were produced on a ram extruder at a pressing pressure of 50 bar and these were dried for 4 hours at 120° C. and calcined for 16 hours at 500° C.

The finished extrudates had a BET surface area of 661 m²g⁻¹ and a distinctly bimodal pore size distribution with maxima at about 25 Å and from 80 Å to 90 Å.

Catalyst C: Ce/Si-MPO 40 g of catalyst B in extrudate form were dried overnight at 120° C. and subsequently admixed with a solution of 2.5 g of Ce(NO₃)₃.6H₂O in 48 ml of distilled water. After allowing to stand for half an hour, the water was taken off at 80° C. and the extrudates were dried for 2 hours at 120° C. and calcined for 2 hours at 540° C.

The finished extrudates contained 1.9% by weight of cerium.

Catalyst D: Si-Al-MPO

A 10 l flask was charged with 505 g of tetraethyl orthosilicate (Si(OC₂H₅)₄), 6.34 g of aluminum isopropoxide (Al(O-isoC₃H₇)₃), 146.4 g of isopropanol and 720 g of ethanol and the mixture was homogenized for 30 minutes. A mixture of 120 g of dodecylamine, 1560 g of distilled water and 17.5 g of 10% strength hydrochloric acid was slowly added dropwise while stirring over a period of 30 minutes. The resulting white suspension was stirred for 20 hours at about 300 rpm, filtered and the solid was washed with distilled water until neutral. After drying for 24 hours at 60° C., the product was calcined for 5 hours at 500° C. The powder had a BET surface area of 990 m²g⁻¹ and contained 43% by weight of silicon and 0.53% by weight of aluminum.

70 g of the Si—Al oxide were compacted together with 46 g of boehmite and 2 g of formic acid in a kneader and kneaded for 120 minutes with addition of water. 2 mm extrudates were produced on a ram extruder at a pressing pressure of 40 bar and these were dried for 16 hours at 110° C. and calcined for 16 hours at 500° C.

The finished extrudates had a BET surface area of 641 m²g⁻¹ and a distinctly bimodal pore size distribution with maxima at about 30 Å and from 60 to 200 Å.

Catalyst E: SiO₂, low surface area (comparative example)

SiO₂ was precipitated from water glass by acidification with sulfuric acid. After filtration, the powder was spray dried, extruded to form 3 mm extrudates and these were calcined at 650° C. The surface area of the calcined extrudates was 173 m²g⁻¹.

Catalyst F: MCM-41 (as described in J. Am. Chem. Soc., 114 (1992), page 10834)

115.5 g of tetramethylammonium bromide was added to 1500 ml of cetyltrimethylammonium chloride solution [25% by weight of C₁₆H₃₃N(CH₃)₃Cl] and stirred for 30 minutes. Subsequently, 272.6 g of sodium silicate, 30 g of sodium aluminate, 187.5 g of Aerosil® 200 and 1500 ml of water were slowly added. The mixture was transferred to an autoclave and stirred for 16 hours at room temperature. The mixture was then heated without stirring to 160° C. and crystallized for 3 days. After filtering off and washing the solid, it was calcined for 12 hours at 500° C. The powder had a BET surface area of 640 m²g⁻¹, an SiO₂/Al₂O₃ ratio of 30:1 and pores of about 43 Å.

100 g of MCM-41 (powder prepared above) were admixed with 67 g of boehmite and 3 g of formic acid, compacted in a kneader and kneaded for 45 minutes with addition of water (150 ml). 2 mm extrudates were produced on a ram extruder at a pressing pressure of 80 bar and these were dried for 16 hours at 110° C. and calcined for 16 hours at 500° C.

Amination examples

The experiments were carried out in a tube reactor (6 mm internal diameter) under isothermal conditions at from 260° to 300° C. and a pressure of 280 bar using a mixture of isobutene and ammonia in a molar ratio of 1:1.5. The reaction products were analyzed by gas chromatography.

The results are shown in Table 1 and demonstrate that the catalysts of the present invention give significantly higher yields than oxide-based catalysts prepared by conventional methods and that, in particular, the activity can be further increased by cerium impregnation.

TABLE 1 tert-Butylamine (NH₃: C₄H₈ = 1.5)

| Catalyst | | | | tert-Butylamine yield [% by weight] | | | |
|---|---|---|---|---|---|---|---|
| No. | Al₂O₃ [% by weight] | Pressure [bar] | Temperature [°C.] | WHSV 0.7 [g/g · h] | WHSV 1.5 [g/g · h] | WHSV 3 [g/g · h] | Bulk density [kg/l] |
| A | 40 | 280 | 300 | 12.24 | 11.47 | 9.60 | 0.39 |
| B | 40 | 280 | 300 | 12.48 | 11.75 | 9.61 | 0.42 |
| C | 40 | 280 | 300 | 12.17 | 12.18 | 11.44 | 0.42 |
| D | 40 | 280 | 300 | 11.88 | 11.46 | 10.27 | 0.28 |
| E |  | 280 | 300 | 2.01 | 0.92 | 0.52 | 0.37 |
| F | 40 | 280 | 300 | 12.86 | 11.20 |  | 0.54 |

We claim:

1. A process for preparing amines of the formula I

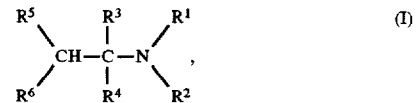

where

R¹,R²,R³,R⁴,R⁵,R⁶ are hydrogen, C₁–C₂₀-alkyl, C₂–C₂₀-alkenyl, C₂–C₂₀-alkynyl, C₃–C₂₀-cycloalkyl, C₄–C₂₀-alkyl-cycloalkyl, C₄–C₂₀-cycloalkyl-alkyl, aryl, C₇–C₂₀-alkylaryl or C₇–C₂₀-aralkyl, R¹ and R² together form a saturated or unsaturated, divalent C₃–C₉-alkylene chain and R³ and R⁵ are C₂₁–C₂₀₀-alkyl, C₂₁–C₂₀₀-alkenyl or together form a divalent C₂–C₁₂-alkylene chain, by reacting olefins of the formula II

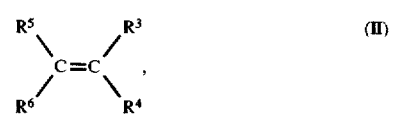

where R³, R⁴, R⁵ and R⁶ are as defined above, with ammonia or primary or secondary amines of the formula III

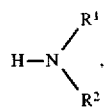

where $R^1$ and $R^2$ are as defined above, at from 200° to 350° C. and a pressure of from 100 to 300 bar in the presence of a heterogeneous catalyst, wherein the heterogeneous catalysts are mesoporous oxides having a high surface area, having a characteristic step in the relative pressure range of $p/p°=0.2.-0.4$ in an isotherm measured by means of nitrogen adsorption (77K); having mesopores present in the range of 2 to 6 nm; having X-ray crystallographic reflections in the 2-theta range from 2° to 6°, and having a surface area in the powder form of from 400 to 1400 $m^2g^{-1}$ determined by the BET method.

2. The process for preparing amines I of claim 1, wherein the amine I formed is separated off and the unreacted starting materials II and III are recirculated.

3. The process for preparing amines of claim 1, wherein the olefin II used is isobutene, diisobutene, cyclopentene, cyclohexene or polyisobutene.

4. The process for preparing amines of claim 1, wherein the heterogeneous catalysts used are mesoporous oxides having a high surface area which are composed of one or more oxides selected from the group consisting of $SiO_2$, $Al_2O_3$, $B_2O_3$, $Ga_2O_3$, $In_2O_3$, $TiO_2$, $ZrO_2$, $Nb_2O_5$, $Fe_2O_3$, $GeO_2$, $SnO_2$, $CeO_2$ or $ThO_2$.

5. The process for preparing amines of claim 1, wherein the heterogeneous catalysts used are mesoporous oxides having a high surface area which are essentially free is of alkali metal or alkaline earth metal ions.

6. The process for preparing amines of claim 1, wherein the heterogeneous catalysts used are mesoporous oxides having a high surface area which are doped with one or more transition metals.

7. The process for preparing amines of claim 1, wherein the heterogeneous catalysts used are mesoporous oxides having a high surface area which are doped with one or more elements of the rare earths.

8. The process for preparing amines of claim 1, wherein the heterogeneous catalysts used are mesoporous oxides having a high surface area which have been treated with an acid, in particular an acid selected from the group consisting of hydrochloric acid, hydrofluoric acid, sulfuric acid, phosphoric acid, oxalic acid or mixtures thereof.

9. The process for preparing amines of claim 1, wherein the heterogeneous catalysts comprising mesoporous oxides having a high surface area are shaped using a binder and calcined at from 200° to 600° C.

10. The process for preparing amines of claim 1, wherein the heterogeneous catalysts are mesoporous oxides having a surface area of from more than 600 $m^2g^{-1}$, measured by the BET method.

11. The process for preparing amines of claim 1, wherein the mesoporous oxides having a high surface area are of the MCM-41 type.

* * * * *

UNITED STATES PATENT AND TRADEMARK OFFICE
CERTIFICATE OF CORRECTION

PATENT NO. : 5,780,680

DATED : July 14, 1998

INVENTOR(S) : ELLER et al.

It is certified that error appears in the above-identified patent and that said Letters Patent is hereby corrected as shown below:

Column 10, claim 5, line 1, delete "is".

Column 10, claim 10, line 24, delete "from".

Signed and Sealed this

Fifteenth Day of September, 1998

Attest:

BRUCE LEHMAN

*Attesting Officer*    *Commissioner of Patents and Trademarks*